(12) United States Patent
Thompson, Jr. et al.

(10) Patent No.: US 9,849,001 B2
(45) Date of Patent: *Dec. 26, 2017

(54) BIO-MECHANICAL FINGER BRACE ASSEMBLY

(71) Applicant: RCM Enterprise, LLC, Tumwater, WA (US)

(72) Inventors: Robert Thompson, Jr., Olympia, WA (US); Jon Bengtsson, Olympia, WA (US); Anthony Charles Peto, Olympia, WA (US); Charles Colin Macduff, Olympia, WA (US); Sydney Tye Minnis, Seattle, WA (US); Eric Dennis Klumper, Boulder, CO (US); Bradley Arthur Crittenden, Olympia, WA (US)

(73) Assignee: RCM Enterprise, LLC, Olympia, WA (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/013,907

(22) Filed: Feb. 2, 2016

(65) Prior Publication Data

US 2017/0020691 A1    Jan. 26, 2017

Related U.S. Application Data

(60) Provisional application No. 62/111,506, filed on Feb. 3, 2015, provisional application No. 62/115,119, filed on Feb. 11, 2015.

(51) Int. Cl.
*A61F 2/54*  (2006.01)
*A61F 2/58*  (2006.01)
(Continued)

(52) U.S. Cl.
CPC ................ *A61F 2/586* (2013.01); *A61F 2/76* (2013.01); *A61F 5/013* (2013.01); *A61F 2220/0091* (2013.01)

(58) Field of Classification Search
CPC .... A61F 2/54; A61F 2/58; A61F 2/586; A61F 5/013
See application file for complete search history.

(56) References Cited

U.S. PATENT DOCUMENTS

| 319,776 A | 6/1885 | Bashore |
| 984,179 A | 2/1911 | Aydt |

(Continued)

FOREIGN PATENT DOCUMENTS

| GB | 2488365 | 8/1912 |
| GB | 110333 | 10/1917 |
| JP | 2002345861 | 12/2002 |

OTHER PUBLICATIONS

International Search Report and Written Opinion dated Nov. 4, 2016 for Int. Application No. PCT/US2016/048758, 7 pp.
(Continued)

*Primary Examiner* — Bruce E Snow
(74) *Attorney, Agent, or Firm* — James A. Sheridan; Sheridan Law, LLC

(57) ABSTRACT

The disclosure provides apparatus and methods of use pertaining to a biomechanical finger brace assembly. In one embodiment, the assembly includes a coupling tip, a proximal ring configured to concentrically receive a user's finger, a distal ring configured to concentrically receive the finger, and a rocker formed in an H-shape. The distal ring and the rocker are pivotally suspended between a proximal coordinated pivot point anchored on the proximal ring and a distal coordinated pivot point anchored on the coupling tip, such that movements of the finger within the proximal ring articulate the distal ring together with the rocker to articulate the coupling tip. The coupling tip may include an open end or an enclosed recess to accept a minimally-amputated or non-amputated finger. Other embodiments are also disclosed.

12 Claims, 13 Drawing Sheets

(51) Int. Cl.
*A61F 5/01* (2006.01)
*A61F 2/76* (2006.01)

(56) References Cited

U.S. PATENT DOCUMENTS

| | | | |
|---|---|---|---|
| 2,706,296 | A | 4/1955 | Fletcher |
| 2,867,819 | A | 1/1959 | George |
| 3,483,718 | A | 12/1969 | Lodrini |
| 3,707,963 | A | 1/1973 | Keropian |
| 4,258,441 | A | 3/1981 | Bell |
| 4,813,406 | A | 3/1989 | Ogle, II |
| 4,997,433 | A | 3/1991 | Goble et al. |
| 5,062,855 | A | 11/1991 | Rincoe |
| 5,941,914 | A | 8/1999 | Jacobsen et al. |
| 6,416,703 | B1 | 7/2002 | Kristinsson et al. |
| 6,908,489 | B2 | 6/2005 | Didrick |
| 8,337,568 | B2 | 12/2012 | Macduff |
| 9,375,319 | B2 | 6/2016 | Macduff |
| 2004/0054424 | A1 | 3/2004 | Matsuda |
| 2005/0043822 | A1 | 2/2005 | Didrick |
| 2006/0212129 | A1 | 9/2006 | Lake et al. |
| 2006/0224249 | A1 | 10/2006 | Winfrey |
| 2008/0127768 | A1 | 6/2008 | Shirai et al. |
| 2008/0262636 | A1 | 10/2008 | Puchhammer |
| 2010/0042229 | A1 | 2/2010 | Hawk |
| 2010/0082103 | A1 | 4/2010 | Blunn et al. |
| 2010/0191343 | A1 | 7/2010 | Puchammer et al. |
| 2010/0262057 | A1 | 10/2010 | Chandrasekhar et al. |
| 2011/0144770 | A1 | 6/2011 | Moyer et al. |
| 2011/0208322 | A1 | 8/2011 | Rifkin, Jr. et al. |
| 2012/0146352 | A1 | 6/2012 | Haslinger |
| 2012/0303136 | A1 | 11/2012 | MacDuff |
| 2012/0330432 | A1 | 12/2012 | Fong |
| 2013/0226315 | A1 | 8/2013 | Varley |
| 2013/0268094 | A1 | 10/2013 | Van Wiemeersch |
| 2014/0078118 | A1 | 3/2014 | Robb |
| 2014/0202741 | A1 | 10/2014 | Macduff |
| 2014/0303749 | A1 | 10/2014 | Macduff |
| 2014/0303750 | A1 | 10/2014 | Macduff |
| 2014/0371897 | A1 | 12/2014 | Lin et al. |
| 2015/0138968 | A1 | 9/2015 | Hunter |

OTHER PUBLICATIONS

Pop, S., "Finger Prosthetic Shows Perfect Balance Between Flexibility and Sturdiness—Gallery", Oct. 23, 2014, 9 pp.
International Search Report and Written Opinion for Int. Appl. No. PCT/US2016/016219, dated Jun. 10, 2016, 6 pp.
International Search Report and Written Opinion for Int. Appl. No. PCT/US2016/016223, dated Jun. 2, 2016, 12 pp.
Leow, M., et al. "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.
Cabibihan, J. "Patient-Specific Prosthetic Fingers by Remote Collaboration—a Case Study", PLoS ONE, May 2011, vol. 6, No. 5.
International Search Report and Written Opinion for PCT/US16/16215, dated Apr. 22, 2016, 8 pp.
International Search Report and Written Opinion for Appl. No. PCT/US2016/032721, dated Aug. 26, 2016, 20 pp.
International Search Report and Written Opinion for Appl. No. PCT/US2016/032732, dated Aug. 25, 2016, 11 pp.
Pop, S., "Finger Prosthetic Shows Perfect Balance Between Flexibility and Sturdiness—Gallery", Oct. 23, 2014, 8 pp. as downloaded on Jul. 12, 2017.

BIO-MECHANICAL FINGER BRACE ASSEMBLY

REFERENCE TO PENDING PRIOR PATENT APPLICATION

The application claims the benefit under 35 U.S.C. 119 (e) of U.S. Provisional Patent Application Nos. 62/111,506, filed Feb. 3, 2015 by Jon Bengtsson, Robert Thompson, and Charles Colin Macduff for "BIO-MECHANICAL FINGER BRACE ASSEMBLY," and 62/115,119, filed Feb. 11, 2015 by Robert Thompson and Jon Bengtsson for "BIO-MECHANICAL FINGER ASSEMBLY WITH A DISTAL PHALANGES COMPONENT," both of which patent applications are hereby incorporated herein by reference.

BACKGROUND

If a person loses finger mobility, finger functionality, or all or a segment of his or her physical finger, the result is impaired performance of the hand. Having an amputated or minimally functioning finger (e.g., due to nerve damage, excessive scar tissue, neurological damage or disorders, or other bone or musculature dysfunctionalities) inhibits the person from performing some of the most basic tasks. For example, with one or more dysfunctional fingers, the task of typing on a computer keyboard or dialing on a telephone becomes significantly more difficult. These types of tasks require precise actions that only fingers are able to offer.

Not only do fingers allow for the performance of precise physical actions, they also provide an increased ability to grip or handle items. While holding an item in the hand, the weight of the item is dispersed through all of a user's fingers. By varying the force used by each finger on the holder's hand, the holder is able to manipulate the item in a myriad of ways. However, if the holder is missing all or even part of a single digit, or if a digit is present but nonfunctioning, this freedom of manipulation and the number of degrees through which the holder can manipulate the item is drastically decreased.

Current prosthetic finger and finger brace/support solutions demonstrate several drawbacks. First, a primary category of prosthetics are designed to be worn passively and offer a realistic look. They provide little to no functionality and do not enable the owner to restore functionality to his or her hand. Other prosthetics offer the user some level of restored functionality, but are complex in design and electrically powered. These prosthetics, while perhaps better than going without, are impractical in that they require an external power source and can be both bulky and unwieldy for the user to manage. Still other prosthetic fingers and/or braces are body-powered but lack the design flexibility necessary to accommodate any length of residual finger (e.g., all or partially amputated and varying degrees of amputation) while providing maximum dexterity, grip strength, and finger articulation in an attractive, low-profile device.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a biomechanical brace assembly for a user's residual digit, where a residual digit may include a partially amputated finger or a non-amputated finger. The biomechanical brace includes (1) a coupling tip; (2) a proximal ring configured to concentrically receive the residual digit with a snug fit; (3) a distal ring configured to concentrically receive the residual digit with a snug fit; and (4) a rocker. The distal ring and the rocker are pivotally suspended between a proximal coordinated pivot point anchored on the proximal ring and a distal coordinated pivot point anchored on the coupling tip.

Another embodiment provides a biomechanically driven brace assembly for a user's residual finger. The brace assembly includes (1) a distal ring configured to fit snugly about a middle phalanx of the finger in a ring-like manner; (2) a coupling tip directly coupled with the distal ring via a first hinged connection; (3) a proximal ring configured to fit snugly about the proximal phalanx of the finger in a ring-like manner, where the proximal ring is directly coupled with the distal ring via a second hinged connection; and (4) a rocker indirectly coupled with the distal ring via a third hinged connection with the coupling tip and a fourth hinged connection with the proximal ring. The first and second hinged connections define a midline relative to a z-axis. The third hinged connection is located below the midline, and the fourth hinged connection is located above the midline, such that a relative rotational motion between the proximal ring and the distal ring causes a relative rotational motion between the distal ring and the coupling tip to emulate a finger's natural closing motion.

Yet another embodiment provides a method of fitting a customized biomechanically driven brace assembly having a proximal ring and a distal ring, each configured to accept a user's residual finger. The method includes (1) sliding the assembly onto the residual finger such that the proximal ring encircles a proximal phalanx of the finger and the distal ring encircles a middle phalanx of the finger; (2) assessing a tightness of the proximal ring about the proximal phalanx and the distal ring about the middle phalanx; (3) removing the assembly from the residual finger; (4) selecting, from a plurality of shims having different thicknesses, at least a first shim; and (5) inserting the first shim into an interior of the proximal ring or the distal ring such that the first shim lines at least a portion of an interior of the proximal ring or at least a portion of an interior of the distal ring. The proximal and distal rings may each include one or more shim-retainment apertures, and each of the plurality of shims may include one or more retaining grommets, where the step of inserting the first shim into the interior of the proximal ring or the interior of the distal ring comprises inserting the retaining grommets of the first shim into the shim-retainment apertures of the proximal ring and/or the distal ring.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
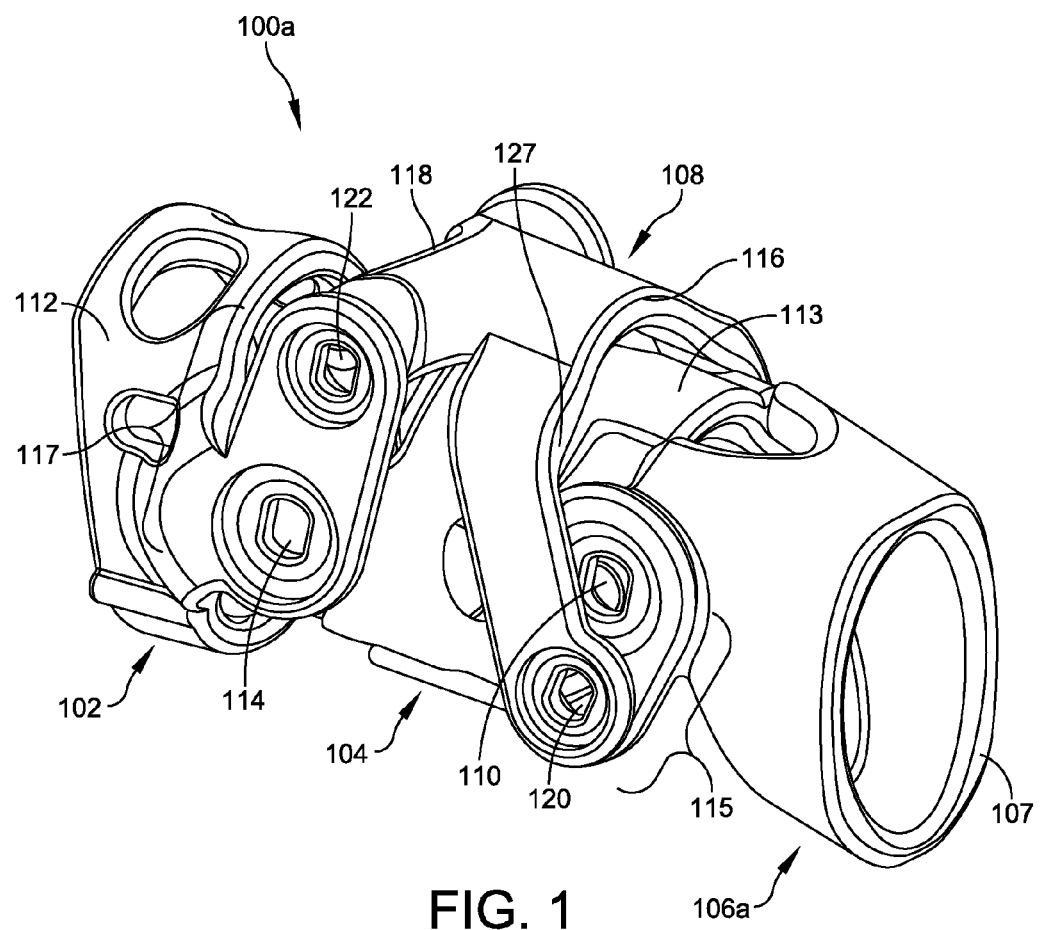
FIG. 1 illustrates a perspective view of one embodiment of a biomechanical finger brace featuring a coupling tip having an open end.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments disclosed herein relate to a custom-designed, self-contained, biomechanically driven finger brace that can be fitted for a user with a fully-formed but injured, sensitive, or dysfunctional finger, or an amputated fingertip or finger segment. The streamlined, sophisticated, and biomechanically driven design allows for a patient with any level of residual finger to utilize a mechanical brace that mimics the motions and functionalities of a real finger. The natural action of the finger brace assembly allows users to regain maximum control of the flexion and extension movements of a fully functioning finger and fingertip and is designed to articulate in a realistic, natural manner in response to movement in the user's own finger or adjacent fingers.

Embodiments described herein include an H-shaped rocker and a recessed coupling tip, both discussed in detail below, that allow the biomechanical finger brace to anchor to any length of residual finger, including an amputation of a fingertip, one or more finger segments, or a non-amputated finger, while protecting the finger against further injury or hypersensitivity and providing the individual user with maximum fit and use flexibility, dexterity, grip strength, and articulation. As a result, the finger brace offers patients experiencing loss of digit function, as well as partial digit amputees, a functional solution that eases the transition back into daily activities, no matter how intricate.

FIGS. 1-4 illustrate perspective, top, side, and front views of one embodiment of a biomechanical finger brace 100a, respectively. In this embodiment, biomechanical finger brace 100a may include four major interconnected components that extend from a proximal end located at the patient's hand to a distal end located at a distance from the patient's hand. These components include a proximal ring 102, a distal ring 104, a coupling tip 106a, and an H-shaped rocker 108. Proximal ring 102 and distal ring 104 may each have a respective body 112, 113. In this embodiment, bodies 112, 113 may form circular or ring shapes that are configured to anchor onto a user's residual finger. More specifically, body 112 of proximal ring 102 may be configured to anchor about a proximal phalanx of a user's residual finger with a snug fit. Similarly, body 113 of distal ring 104 may be configured to anchor about a middle phalanx of a user's residual finger with a snug fit.

Figure 2:
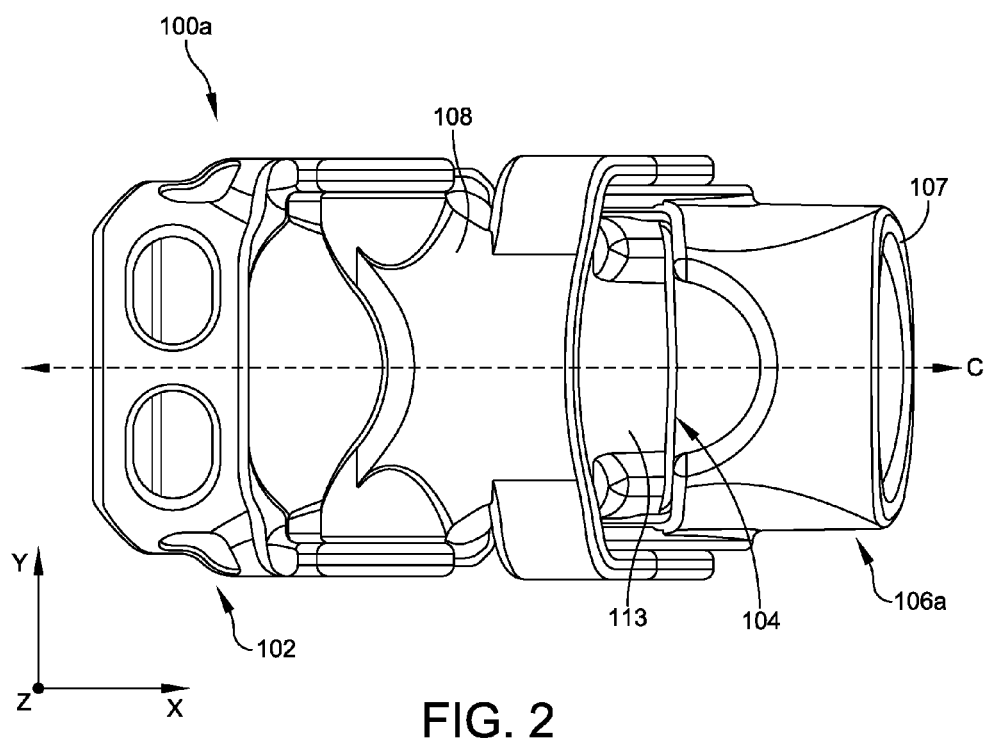
FIG. 2 illustrates a top view of the biomechanical finger brace of FIG. 1, with a centerline axis bisecting the brace relative to a y-axis.

A series of hinges may be used to secure the four primary components in a manner that pivotally suspends distal ring 104 and rocker 108 between coupling tip 106a and proximal ring 102. In one embodiment, these rotative connections may be particularly positioned with respect to a pair of axes detailed in FIGS. 2-3. More specifically, FIG. 2 depicts a centerline, C, that bisects finger brace 100a relative to a y-axis, and FIG. 3 shows a midline, M, that intersects a first hinged connection 110 and a second hinged connection 114, both detailed below, relative to a z-axis.

Figure 3:
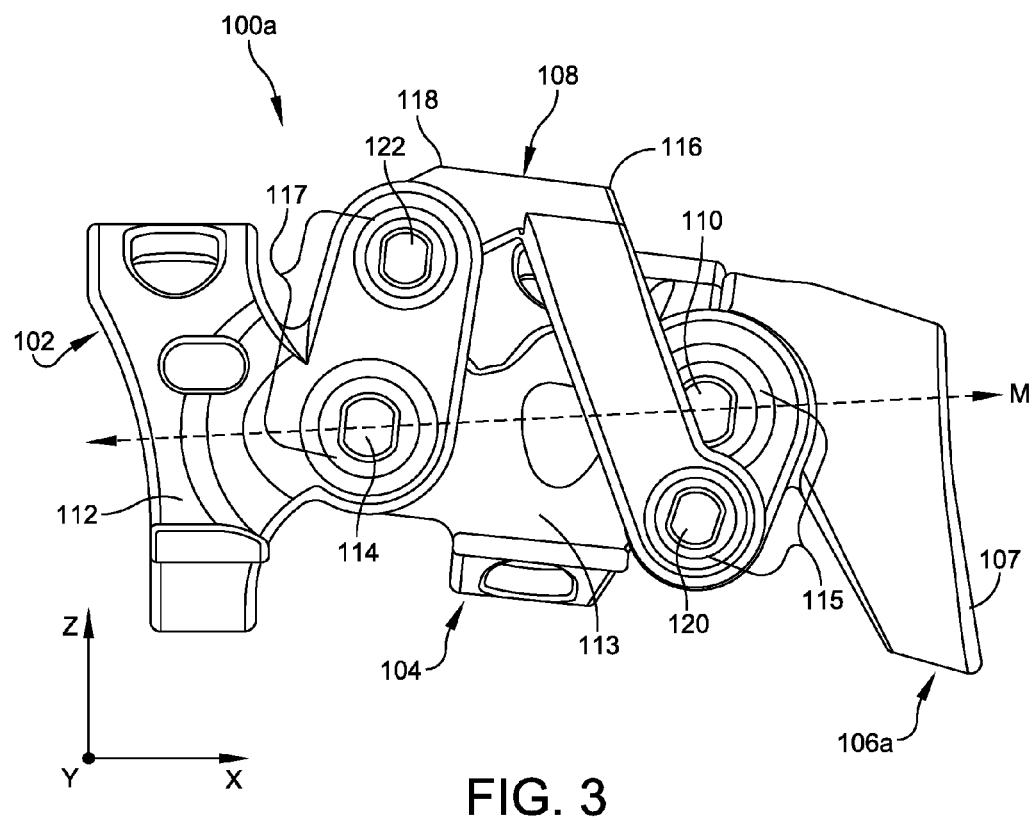
FIG. 3 illustrates a left-side view of the biomechanical finger brace of FIGS. 1 and 2, with a midline axis intersecting first and second hinged connections relative to a z-axis.
Figure 4:
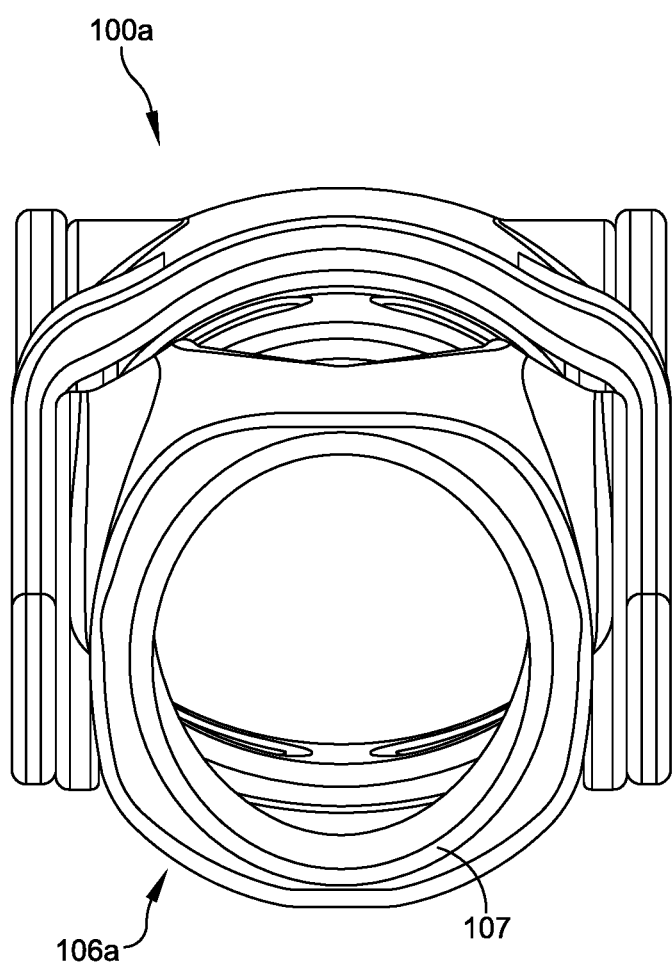
FIG. 4 illustrates a front view of the biomechanical finger brace of FIGS. 1-3.

Turning to the various rotative connections shown in FIGS. 1-3, distal ring 104 may rotatively couple with coupling tip 106a via first hinged connection 110, which may include a pair of parallel pivotal hinges that are symmetric about centerline, C, discussed above in relation to FIG. 2. Each of the pivotal hinges of connection 110 may provide a pivot point between distal ring 104 and coupling tip 106a.

Proximal ring 102 may rotatively couple with distal ring 104 via second hinged connection 114. Second hinged connection 114 may also include a pair of parallel pivotal hinges that are symmetric about the centerline, C, one located on each side of brace 100a such that each provides a pivot point between proximal ring 102 and distal ring 104. As discussed above in relation to FIG. 3, the midline, M, intersects hinged connections 110 and 114, and, therefore, both first and second hinged connections 110, 114 are located directly upon the midline, M, relative to the z-axis.

Rocker 108 may form a H-shape having opposing first and second ends 116, 118, respectively, that extend between coupling tip 106a and proximal ring 102. First end 116 may form a first split prong of the H-shape that rotatively couples with coupling tip 106a via a third hinged connection 120 (FIGS. 1 and 3) located below the midline, M, relative to the z-axis. Second end 118 may form a second split prong of the H-shape that rotatively couples with proximal ring 102 via a fourth hinged connection 122 (FIGS. 1 and 3) located above the midline, M, relative to the z-axis. Both third and fourth hinged connections 120, 122 may include a pair of parallel pivotal hinges that are symmetric about the centerline, C, each providing a pivot point between rocker 108 and coupling tip 106a/proximal ring 102.

To achieve the "suspension" configuration discussed above with respect to distal ring 104 and rocker 108, first and third hinged connections 110, 120 may align to form a distal coordinated pivot point 115, which is anchored upon coupling tip 106a. Similarly, second and fourth hinged connections 114, 122 may align to form a proximal coordinated pivot point 117, which is anchored upon proximal ring 102. While distal ring 104 and rocker 108 do not directly connect to one another, they each directly and pivotally connect with coupling tip 106a and proximal ring 102 via the distal and proximal coordinated pivot points 115, 117, respectively. As a result, distal ring 104 and rocker 108 are each independently, pivotally suspended between coupling tip 106a and proximal ring 102, such that they push and pull in coordinated, yet independent, manners relative to one another. This association of distal ring 104 and rocker 104, without an actual direct link or connection between the two components, allows for more complex, realistic articulation motions of distal ring 104, rocker 108, and coupling tip 106a in response to biomechanical input forces exerted on proximal and distal rings 102, 104.

Any one or more of the first, second, third, and/or fourth hinged connections 110, 114, 120, 122 may be outfitted with hard-stops to prevent hyperextension of brace 100a during operation. For example, a hard-stop 127, shown in FIG. 1, may prevent relative over-rotation of first hinged connection 110, or between distal ring 104 and coupling tip 106a. Mechanical hard-stops may have any appropriate size, shape, and/or configuration.

Working together, proximal ring 102, distal ring 104, coupling tip 106a, and H-shaped rocker 108 form a 4-bar linkage system that allows the coupling tip to be articulated in response to a pulling force on distal ring 104, which places the member in tension and reduces the risk of buckling. Thus, natural movement of the patient's residual finger seated within proximal ring 102 and distal ring 104, or in some cases movement of his or her adjacent fingers, may be used to actuate realistic flexion and extension motions within finger brace 100a. Users may perform their full range of usual activities, including typing, playing a musical instrument, or any other activity that requires the full dexterity of the hand.

The unique and specialized H-shape of rocker 108 allows third hinged connection 120 between rocker 108 and coupling tip 106a to occur outside the assembly, or outside the physical boundary defined by distal ring 104 and coupling tip 106a. This configuration allows users with a relatively longer residual finger, or a relatively long middle phalanx, to take advantage of additional clearance space within the assembly. The user's finger may sit comfortably within and concentric to the brace assembly 100a, while still being protected against further damage and/or hypersensitivity. The concentric design that allows the components of brace 100a to surround or encircle the user's finger, rather than lie above, below, or otherwise adjacent to the finger, provides a low-profile, ergonomic, and attractive device that augments the user's residual finger in the most natural way possible. While rocker 108 is described herein as having an H-shaped profile, it should be understood that rocker 108 may take any appropriate size, shape, type, and/or configuration desired to achieve the functional benefits described above.

Figure 5:
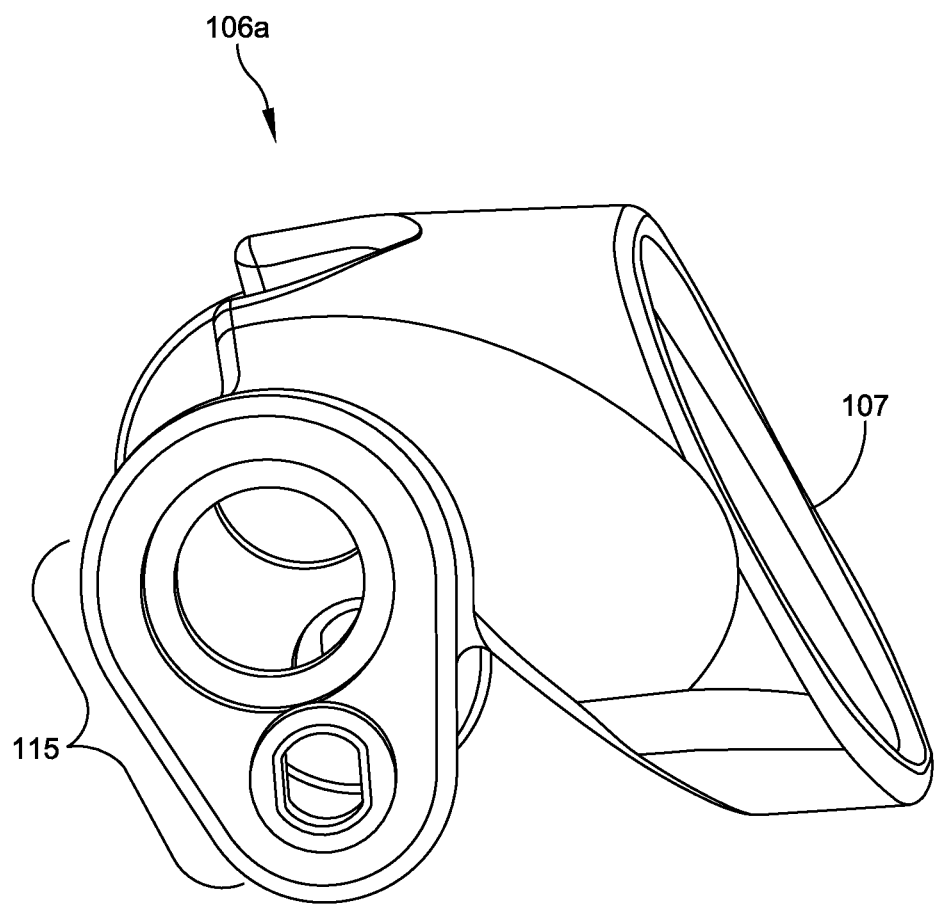
FIG. 5 illustrates a perspective view of one embodiment of the coupling tip of the biomechanical finger brace of FIGS. 1-4.
Figure 6:
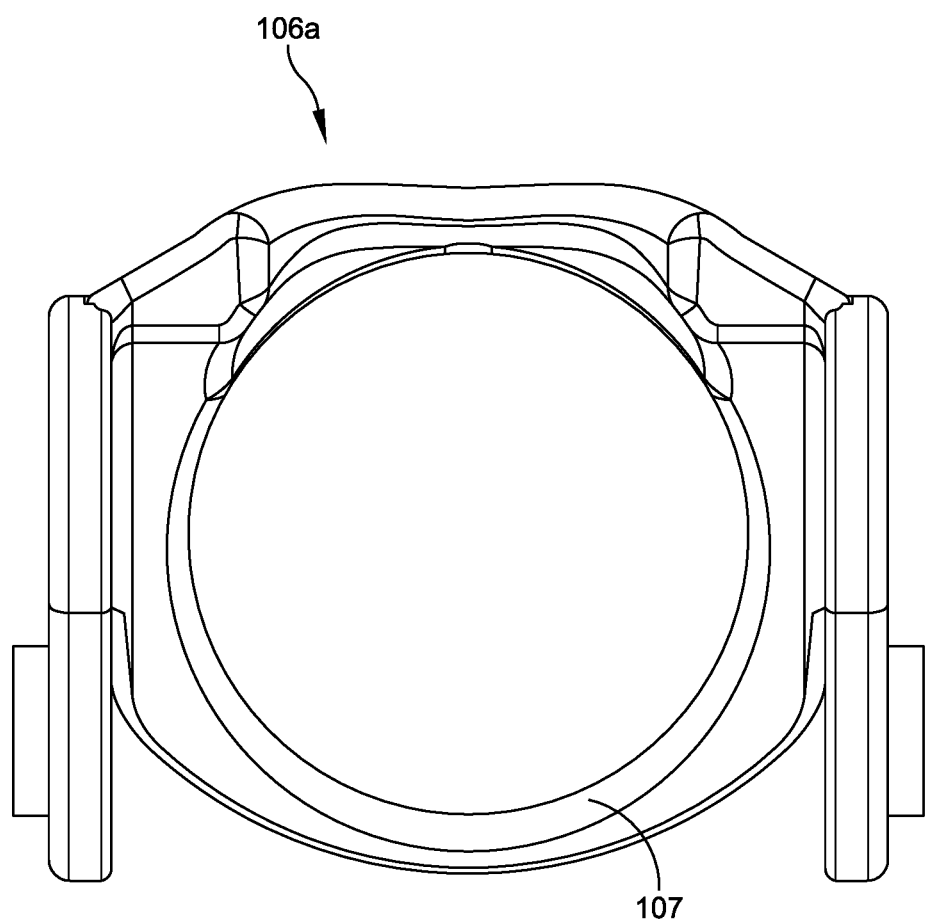
FIG. 6 illustrates a front view of the coupling tip of FIG. 5.
Figure 7:
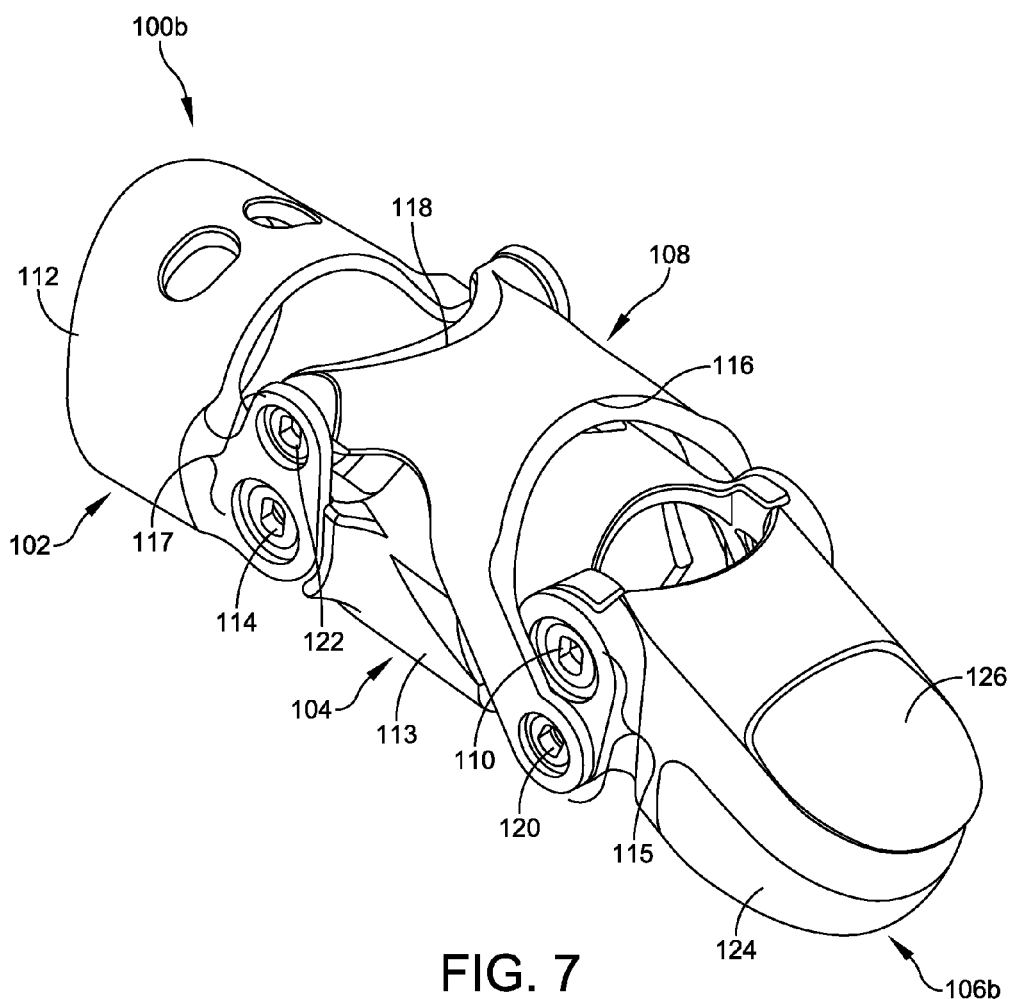
FIG. 7 illustrates a perspective view of another embodiment of a biomechanical finger brace featuring a coupling tip having a recessed end to receive a fingertip.
Figure 8:
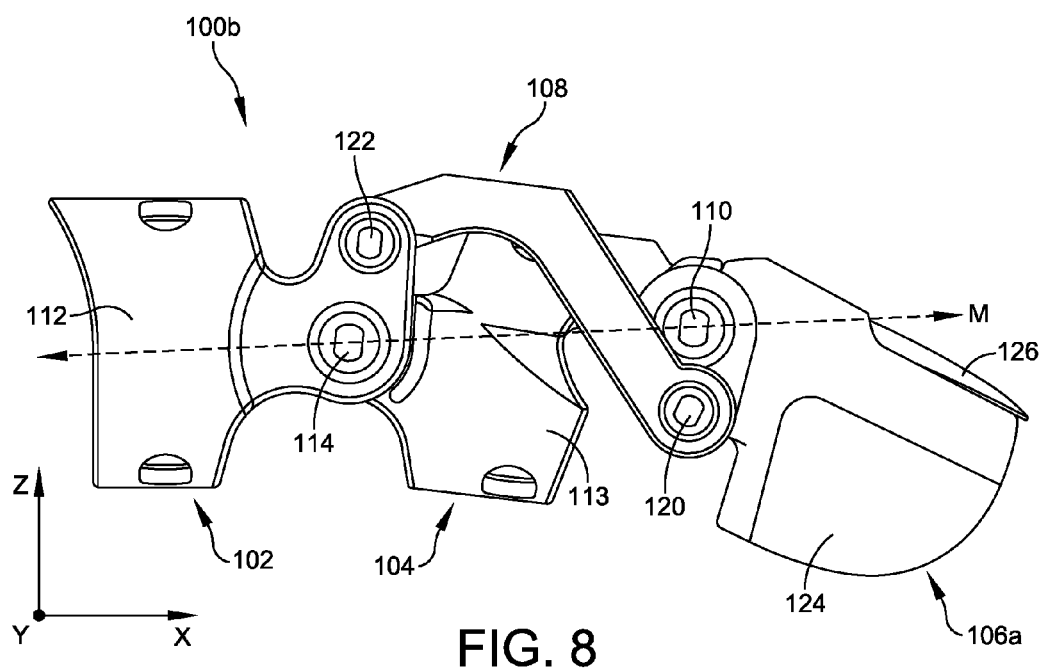
FIG. 8 illustrates a left-side view of the biomechanical finger brace of FIG. 7, with a midline axis intersecting first and second hinged connections relative to a z-axis.
Figure 9:
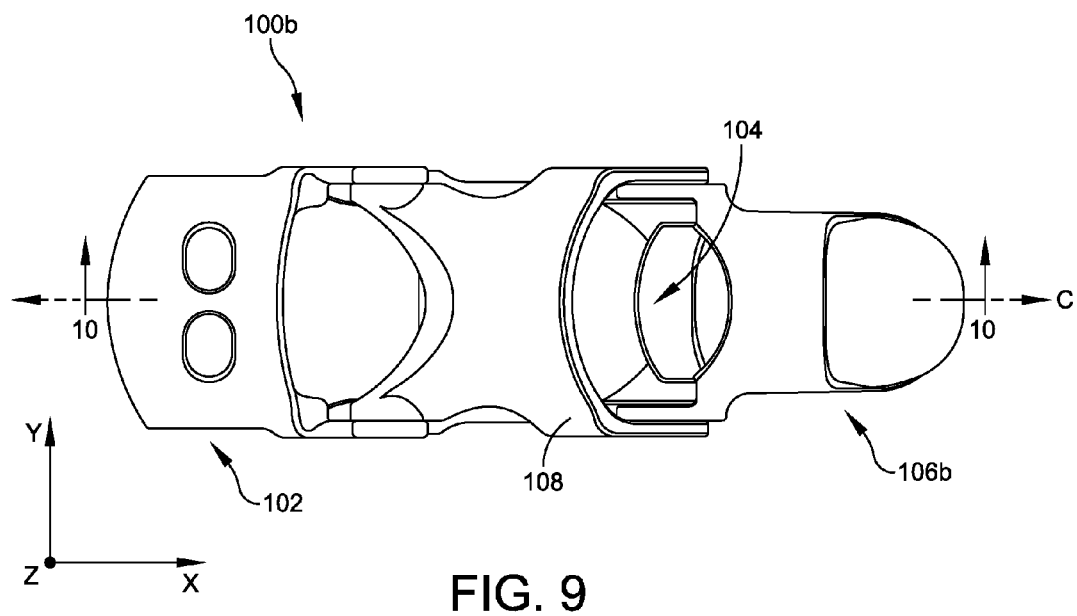
FIG. 9 illustrates a top view of the biomechanical finger brace of FIGS. 7-8, with a centerline axis bisecting the brace relative to a y-axis.
Figure 10:
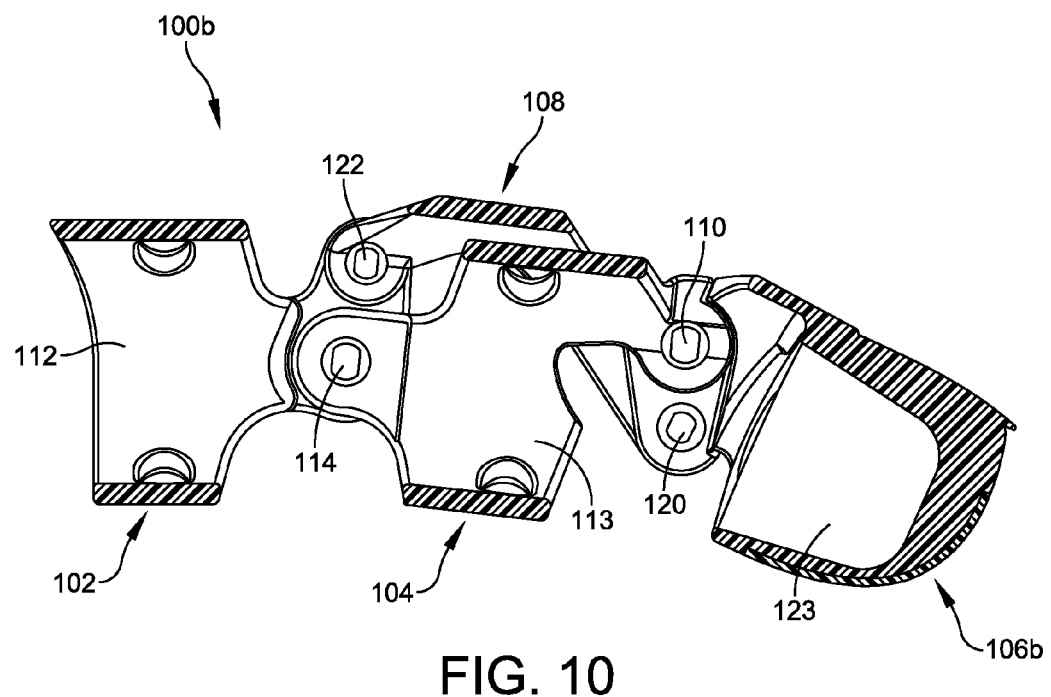
FIG. 10 illustrates a cross-sectional view of the biomechanical finger brace of FIGS. 7-9.
Figure 11:
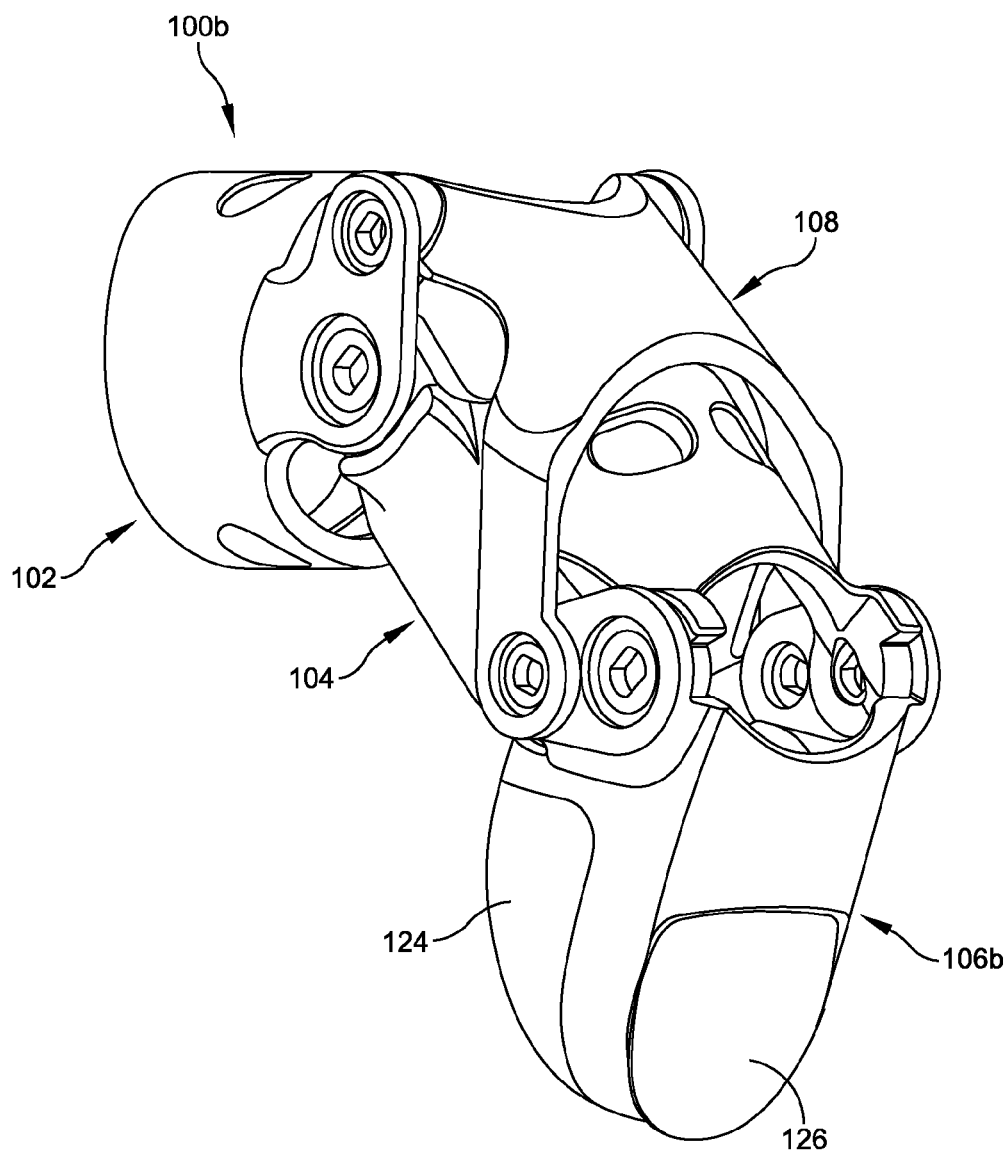
FIG. 11 illustrates another perspective view of the biomechanical finger brace of FIGS. 7-10 in an articulated position.

One embodiment of coupling tip 106a may feature an open end 107, as shown in assembly FIGS. 1-4 and specifically detailed in FIG. 5-6, which illustrate perspective and front views of open coupling tip 106a. In this embodiment, open end 107 may provide a passageway for a finger so as to allow a tip of the finger to emerge from distal ring 104, into and through coupling tip 106a, and out of open end 107 of coupling tip 106a. This embodiment allows brace 100a to function as a therapeutic and/or protective device for a user who has experienced an injury or any type of inhibited articulation functionality to a finger segment, but a very limited amputation or no amputation at all.

FIGS. 7-11 illustrate perspective, side, top, cross-sectional, and perspective-articulated views of another embodiment of a finger brace 100b. In this embodiment, brace 100b may be identical to brace 100a (FIGS. 1-6), with the exception of an alternative coupling tip 106b. Coupling tip 106b may be configured to emulate the aesthetic of an actual fingertip, but may include a hollow recess 123, shown in the cross-sectional view FIG. 10, designed to receive the user's existing fingertip and provide protection against further injury and/or hypersensitivity.

Coupling tip 106b may include a tip pad 124. Tip pad 124 may be formed from a soft-textured silicone or other material that mimics the texture of a real finger. This aids with gripping and provides a softer touch. In one embodiment, a touchscreen mechanism (not shown) may be provided to allow the user to use the brace to operate capacitive touchscreens, which react to the body's natural current. The touchscreen mechanism allows the user to direct his or her own body current through coupling tip 106b of the brace.

One embodiment of coupling tip 106b may also include a nail 126, which mimics a natural edged nail that may provide scratching and peeling functionalities as well as assist with fine-object manipulation.

Embodiments of biomechanical finger brace 100a, 100b are custom designed and individually fitted to accommodate a variety of differing user conditions. In this regard, each finger brace 100a, 100b may be custom manufactured to fit a particular patient or user, providing both custom functionality as well as a mechanical match to the anatomical joint articulation of the user. Design considerations include a number and physiology of joints to be stabilized and other characteristics specific to the individual end user. H-shaped rocker 108 is designed to provide a full-coverage "cage" above and about a patient's finger, thereby protecting the finger from irritation and/or hypersensitivity, without interfering with the supported finger within the biomechanical finger brace 100a, 100b.

To further provide better aesthetics, embodiments of finger brace 100a, 100b may be coated with films and/or colorings matched to the user's skin tone/color. An additive manufacturing process (i.e., 3D printing) facilitates this ability to customize the intricacies of the brace design in order to optimize finger brace 100a, 100b for each patient.

Embodiments of finger brace 100a, 100b may be formed of any suitable structural material that is non-irritating to human skin and allows the user to operate the brace with comfort and confidence. Exemplary materials include titanium, stainless steel, aluminum, silicone, carbon fiber, nylon, plastic/polymer, wood, rubber, gold, silver, tungsten, flex cable, neoprene, or any other suitable material. In one embodiment, components of finger brace 100a, 100b are 3D printed from Duraform EX polymer material.

Using biocompatible materials, various embodiments of finger brace 100a, 100b may be applied as an orthopedic implant that may be surgically implanted into a user's finger. This option may be applied for users having injuries that have crushed their finger bones without the ability to heal or be repaired. In these situations, implantable embodiments of biomechanical finger brace 100a, 100b are able to take the place of the user's original bones without the need for amputation.

Figure 12:
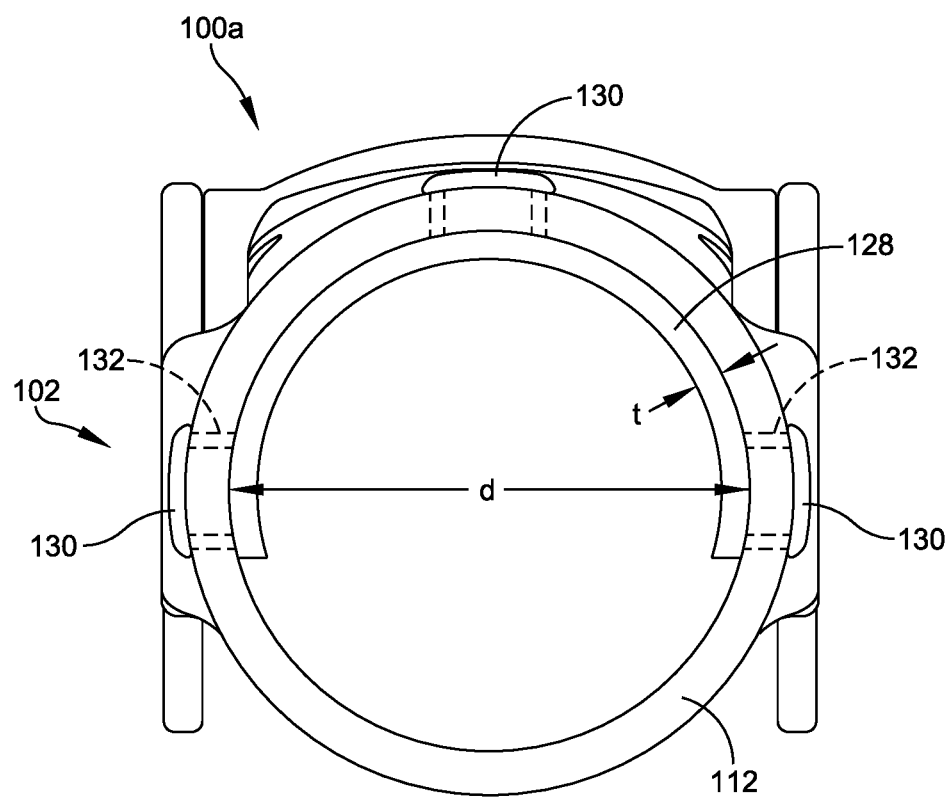
FIG. 12 illustrates an end view of the biomechanical finger brace of FIGS. 1-4 with an inserted shim.

In use, the user may simply slide proximal ring 102 and distal ring 104 of finger brace 100a, 100b onto his or her residual finger, and, if necessary, adjust further using a shim(s). FIG. 12 depicts a rear view of finger brace 100a, in which body 112 of proximal ring 102 is outfitted with a shim 128, which may be employed to allow the sizing of body 112 to account for possible swelling in the fingers, weight gain/loss, or any other post-manufacture changes in the size of the residual finger. While shim 128 is shown inserted into proximal ring 102 of brace 100a, it should be understood that shim 128 applies equally to braces 100a and 100b.

In further detail, a fit kit (not shown) may be provided with each finger brace 100a, 100b and may include a number of shims 128. In this embodiment shown in FIG. 12, shim 128 may approximate a semi-circle or U-shape that abuts an inner diameter, d, of body 112 of proximal ring 102. Shim 128 may have a number of retaining grommets 130 configured to protrude through corresponding shim-retainment apertures 132 within body 112 of proximal ring 102. In other embodiments, shims may form a lesser arc, a full ring, or any other appropriate shape. Each shim 128 may have a different thickness, t, thereby allowing the user to essentially adjust the inner diameter, d, of body 112 of proximal ring 102 in a number of increments as required by the user.

Once finger brace 100a, 100b (adjusted or otherwise) is in place, the user may utilize his or her natural finger movements. The rotatively coupled components of finger brace 100a, 100b will articulate using the same cognitive process that was previously utilized for the original finger. If a user wears multiple braces 100a, 100b, each may be individually operated.

Figure 13:
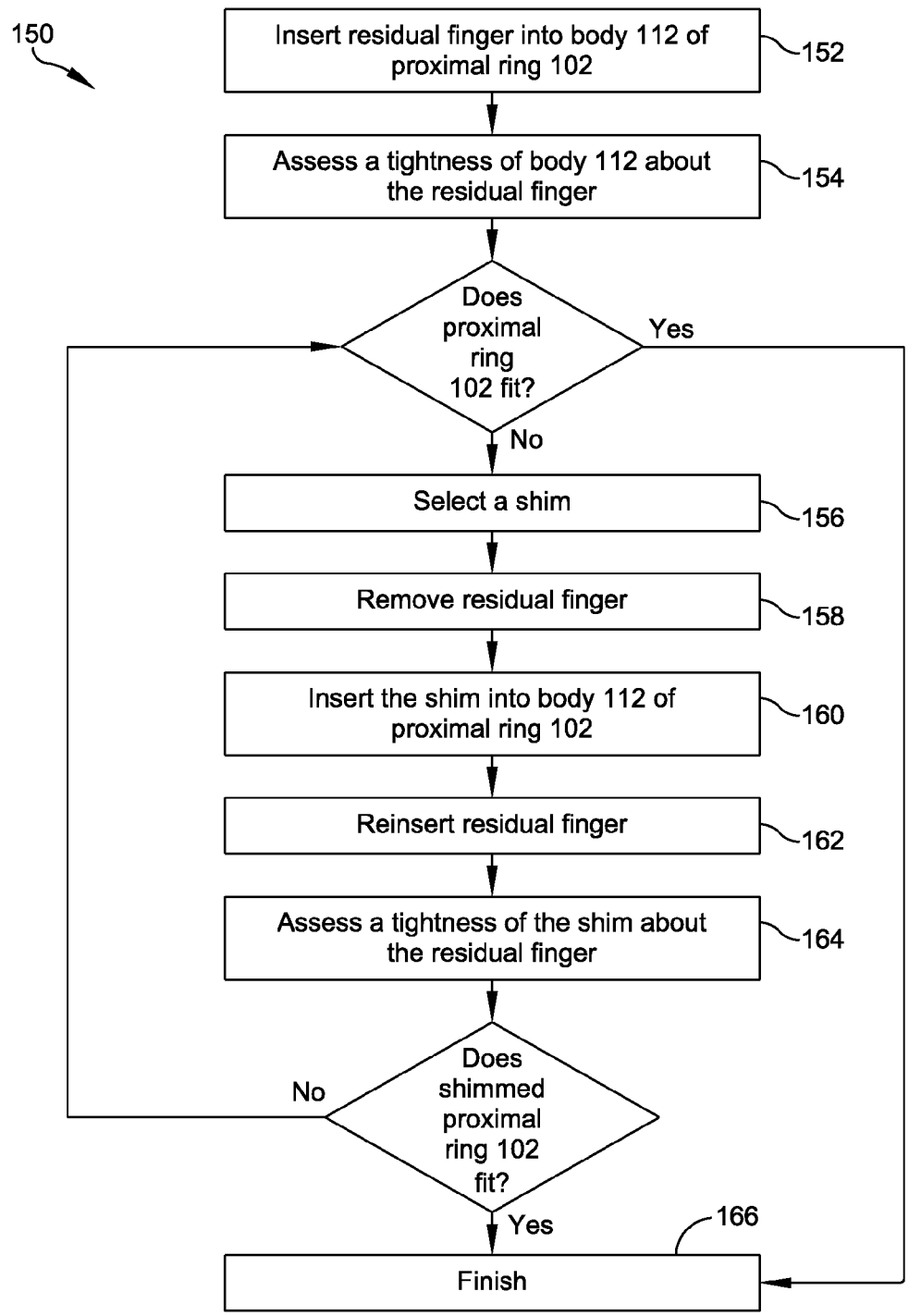
FIG. 13 illustrates a flow chart depicting an exemplary method of fitting the biomechanical finger braces of FIGS. 1-4 and 7-11.

FIG. 13 provides a flow chart depicting an exemplary method 150 for installing and adjusting, or fitting, one embodiment of proximal ring 102 of finger brace 100a, 100b upon a user's finger. Notably, distal ring 104 may be adjusted in a manner similar to that discussed below in relation to proximal ring 102 and method 150.

The method begins with inserting (152) the finger into body 112 of proximal ring 102 and assessing a tightness (154) of body 112 about the finger. Depending on this assessment (154), the user, a medical professional, or another assistant may select a first shim 128 (156) from the fit kit or another source. The user may then remove the finger (158) from proximal ring 102 and insert first shim 128 (160) into the inner diameter, d, of body 112 such that first shim 128 lines the inner diameter, d, while retaining grommets 130 protrude through shim-retainment apertures 132. Once first shim is installed (160), the user may reinsert the residual finger (162) into proximal ring 102 and assess a tightness (164) of first shim 128 (which now lines body 112 of proximal ring 102) about the residual finger. If the shimmed proximal ring 102 fits, method 150 is complete (166), and the user may proceed to biomechanically drive finger brace 100a. If shimmed proximal ring 102 does not fit, method 150 may return to the step of selecting a shim (156), in which a second shim having a different thickness may be selected before proceeding. The user may experiment with multiple shims of varying thicknesses until an ideal or desired fit is achieved.

Embodiments of the finger brace 100a, 100b described above exhibit numerous unique characteristics and provide a variety of medical benefits. An individual's unique physiology and lifestyle patterns dictate the function and performance expected of his or her hands. Using embodiments of the brace described herein, patients may regain independent control of their hands, whether at work or at play. Each device is custom designed, manufactured for a specific individual, and incorporates features that allow for further fine-tuning and adjustment of fit to account for post-manufacturing fluctuations (e.g., shims), enabling the device to fit the user in a manner that allows for a biomechanically driven, low profile, lightweight, highly functioning return to the user's everyday activities, no matter what those activities might entail. A few examples include typing, playing the piano or another instrument, woodworking, and much more.

Embodiments of the biomechanical finger brace described above are body powered, concentrically designed about the length of the finger, and feature linked components that articulate when the user simply moves his or her braced finger. Beyond allowing for a simple, elegant, and streamlined design that offers strength in the lowest possible profile design, employing the user's own biomechanics to drive embodiments of finger brace 100a, 100b provide a host of medical benefits to the user, including reduced swelling of and increased circulation to the braced finger and the hand as a whole, supporting healthy joints in the injured and adjacent fingers.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A biomechanical brace assembly for a user's residual digit, comprising:
   a coupling tip;
   a proximal ring configured to concentrically receive the residual digit with a snug fit;
   a distal ring configured to concentrically receive the residual digit with a snug fit; and
   a rocker, wherein the distal ring and the rocker are pivotally suspended between two proximal coordinated pivot points anchored on the proximal ring and two distal coordinated pivot points anchored on the coupling tip;
   wherein the distal coordinated pivot points comprise a first hinged connection between the distal ring and the coupling tip and a third hinged connection between the rocker and the coupling tip;
   wherein the proximal coordinated pivot points comprise a second hinged connection between the distal ring and the proximal ring and a fourth hinged connection between the rocker and the proximal ring; and
   wherein the rocker defines an H-shape having opposing first and second ends, the first end forming a first split prong at the third hinged connection, and the second end forming a second split prong at the fourth hinged connection.

2. The biomechanical brace assembly of claim 1, wherein:
   the first hinged connection between the distal ring and the coupling tip and the second hinged connection between the distal ring and the proximal ring define a midline relative to a z-axis;
   the third hinged connection between the first split prong of the rocker and the coupling tip is located below the midline; and
   the fourth hinged connection between the second split prong of the rocker and the proximal ring is located above the midline, such that a relative rotational motion between the proximal ring and the distal ring causes a relative rotational motion between the distal ring and the coupling tip to emulate a finger's natural closing motion.

3. The biomechanical brace assembly of claim 2, wherein a centerline bisects the assembly relative to a y-axis, and wherein the first, second, third, and fourth hinged connections each comprise a pair of parallel pivotal hinges that are symmetric about the centerline.

4. The biomechanical brace assembly of claim 1, wherein the coupling tip comprises a recess to accept a fingertip.

5. The biomechanical brace assembly of claim 4, wherein the coupling tip further comprises a tip pad.

6. A biomechanically driven brace assembly for a user's residual finger, comprising:
a distal ring configured to fit snugly about a middle phalanx of the finger in a ring-like manner;
a coupling tip directly coupled with the distal ring via a first hinged connection;
a proximal ring configured to fit snugly about the proximal phalanx of the finger in a ring-like manner, the proximal ring directly coupled with the distal ring via a second hinged connection; and
a rocker indirectly coupled with the distal ring via a third hinged connection with the coupling tip and a fourth hinged connection with the proximal ring, wherein:
the first and second hinged connections define a midline relative to a z-axis;
the third hinged connection is located below the midline; and
the fourth hinged connection is located above the midline, such that a relative rotational motion between the proximal ring and the distal ring causes a relative rotational motion between the distal ring and the coupling tip to emulate a finger's natural closing motion.

7. The biomechanically driven brace assembly of claim 6, wherein the first and third hinged connections align at distal coordinated pivot points on the coupling tip, and wherein the second and fourth hinged connections align at proximal coordinated pivot points on the proximal ring.

8. The biomechanically driven brace assembly of claim 6, wherein when in use, the assembly and the finger are concentric.

9. The biomechanically driven brace assembly of claim 6, wherein the rocker defines an H-shape having opposing first and second ends, the first end forming a first split prong at the third hinged connection, and the second end forming a second split prong at the fourth hinged connection.

10. The biomechanically driven brace assembly of claim 9, wherein a centerline bisects the assembly relative to a y-axis, and wherein the first, second, third, and fourth hinged connections each comprise a pair of parallel pivotal hinges that are symmetric about the centerline.

11. The biomechanically driven brace assembly of claim 6, wherein the coupling tip comprises one of an open end and a recess to accept a fingertip.

12. The biomechanical brace assembly of claim 6, further comprising one or more mechanical hard-stops configured to prevent relative over-rotation at the first, second, third, or fourth hinged connections.

* * * * *